(12) United States Patent
Santra

(10) Patent No.: US 10,085,444 B2
(45) Date of Patent: Oct. 2, 2018

(54) SILICA-BASED ANTIBACTERIAL AND ANTIFUNGAL NANOFORMULATION

(71) Applicant: University of Central Florida Research Foundation, Inc., Orlando, FL (US)

(72) Inventor: Swadeshmukul Santra, Orlando, FL (US)

(73) Assignee: UNIVERSITY OF CENTRAL FLORIDA RESEARCH FOUNDATION, Orlando, FL (US)

( * ) Notice: Subject to any disclaimer, the term of this patent is extended or adjusted under 35 U.S.C. 154(b) by 0 days.

(21) Appl. No.: 14/109,027

(22) Filed: Dec. 17, 2013

(65) Prior Publication Data

US 2017/0118980 A1  May 4, 2017

Related U.S. Application Data

(62) Division of application No. 13/527,691, filed on Jun. 20, 2012, now Pat. No. 8,632,811, which is a division of application No. 12/332,021, filed on Dec. 10, 2008, now Pat. No. 8,221,791.

(51) Int. Cl.
  *A01N 25/32* (2006.01)
  *A01N 59/20* (2006.01)

(52) U.S. Cl.
  CPC ............. *A01N 25/32* (2013.01); *A01N 59/20* (2013.01)

(58) Field of Classification Search
  CPC ................................ A01N 25/32; A01N 59/20
  See application file for complete search history.

(56) References Cited

U.S. PATENT DOCUMENTS

| | | | |
|---|---|---|---|
| 2,913,419 | A | 4/1956 | Alexander |
| 3,983,214 | A | 9/1976 | Misato et al. |
| 3,992,146 | A | 11/1976 | Fazzalari |
| 5,462,738 | A | 10/1995 | LeFiles et al. |
| 5,939,357 | A | 8/1999 | Jones et al. |
| 6,471,976 | B1 | 10/2002 | Taylor et al. |
| 6,548,264 | B1 | 4/2003 | Tan et al. |
| 6,924,116 | B2 | 8/2005 | Tan et al. |
| 7,147,921 | B2 | 12/2006 | Camp et al. |
| 7,163,709 | B2 | 1/2007 | Cook et al. |
| 7,226,610 | B2 | 6/2007 | Winniczuk |
| 7,332,351 | B2 | 2/2008 | Tan et al. |
| 8,221,791 | B1 | 7/2012 | Santra |
| 8,246,933 | B2 | 8/2012 | Jiang et al. |
| 8,361,437 | B2 | 1/2013 | Sharma et al. |
| 2001/0051174 | A1 | 12/2001 | Staats |
| 2003/0213169 | A1* | 11/2003 | Allen .................. 47/58.1 R |
| 2004/0009642 | A1 | 1/2004 | Yoo et al. |
| 2004/0067247 | A1 | 4/2004 | DeSloovere et al. |
| 2004/0091417 | A1 | 5/2004 | Yadav |
| 2004/0096421 | A1 | 5/2004 | Kurihara et al. |
| 2005/0084438 | A1 | 4/2005 | Do et al. |
| 2006/0018966 | A1 | 1/2006 | Lin et al. |
| 2007/0009672 | A1 | 1/2007 | Jeong et al. |
| 2007/0010475 | A1 | 1/2007 | Richardson |
| 2007/0098806 | A1 | 5/2007 | Ismail et al. |
| 2007/0104751 | A1 | 5/2007 | Levar |
| 2007/0140951 | A1 | 6/2007 | O'Brien et al. |
| 2007/0269382 | A1 | 11/2007 | Santra et al. |
| 2009/0131517 | A1* | 5/2009 | Height ................... A01N 25/12 514/495 |
| 2010/0015236 | A1 | 1/2010 | Magdassi et al. |

OTHER PUBLICATIONS

Maniprasad, et al.; Novel Copper (Cu) Loaded Core-Shell Silica Nanoparticles with Improved Cu Bioavailability: Synthesis, Characterization and Study of Antibacterial Properties; Journal of Biomedical Nanotechnology; vol. 8, 1-9, 2012.
Maniprasad, et al.; Antimicrobial Properties of Copper and Silver Loaded Silica Nanomaterials; Manuscript ID No. 1198620; to be submitted to the 36th International Conference on Advanced Ceramics and Composites (ICACC); Apr. 4, 2012.
H.W. Richardson, "Handbook of Copper Compounds and Applications Copper Fungicides/batericides" H.W. Richardson Editor, 1997, Marcel Dekker, Inc.: New York, NY, pp. 93-122.
Torgeson. D.C .. ed. "Fungicides—An Advanced Treatise" Agricultural and Industrial Applications and Enviromental Interaction. vol. 1. 1967. Academic Press: New York. NY, Ch. 6, p. 153-193 [chapter Title: Formulation: Author: E. Somers.
Navarro, E., et al., in "Environmental behavior and ecotoxicity of engineered nanoparticles to algae, plants, and fungi," Ecotoxicology, 2008, 17(5): pp. 372-386.
Oberdorster, G., et al., in Nanotoxicology: An Emerging Discipline Evolving from Studies of Ultrafine Particles, Environmental Health Perspectives, 2005, 113(7): pp. 823-839.
S. Santra, et al., in "Fluorescence Lifetime Measurements to Determine the Core-Shell Nanostructure of FITC-doped Silica Nanoparticles: An Optical Approach to Evaluate Nanoparticle Photostability" Journal of Luminescence, 2006, 117(1) pp. 75-82.
Zhang, K., Synthesis and Characterization of Silica-Copper Oxide Composite Derived from Microemulsion Processing, 1999, Langmuir, vol. 15, pp. 3056-3061.

(Continued)

*Primary Examiner* — Sue X Liu
*Assistant Examiner* — Andriae M Holt
(74) *Attorney, Agent, or Firm* — Arent Fox LLP

(57) ABSTRACT

A silica-based nanoformulation and method is used to treat citrus canker, inhibit the growth of mold and mildew, and add nutrients to soil used for agricultural purposes. The nanotechnology-enabled copper-loaded, silica nanoformulation (CuSiNP/NG) design is a "revolutionary re-invention" of Cu for safe application because it provides a formulation with maximum abundance of ionic Cu, provides sustained and optimal Cu ion release for long-term disease protection, better adherence to plant surfaces and structural surfaces due to gel-based nanostructure of CuSiNG, thus avoiding multiple spray applications and reducing the amount of Cu used in comparison to existing Cu compounds without compromising antibacterial activity. Thus, the silica-based nanoformulation releases copper in non-toxic quantities to the environment and the silica matrix provides an environmentally safe host material with a flexible design that is optimized to provide specific antifungal and antibacterial remediation using infrequent applications.

15 Claims, 10 Drawing Sheets

(56) References Cited

OTHER PUBLICATIONS

Zhang, X. A New Solution Route to Hydrogen-terminated Silicon Nanoparticles: Synthesis, Functionalization and Water Stability, Jan. 2007, Nanotechnology, vol. 18, pp. 1-6.

Kikteva, T.A., Probing the Sol-Gel Conversion in the Tetraethoxysilane/Alcohol/Water System with the Aid of Diffusion-Controlled Flourescence Quenching, 1997, Journal of Colloid and Interface Science, vol. 193, pp. 163-166.

Yeshchenko, Oleg, Influence of Annealing Conditions on Structure and Optical Properties of Copper Nanoparticles Embedded in Silica Matrix, 2006, Physics Department, National Taras Shevchenko Kyiv University, Ukraine, pp. 1-25.

International Search Report and Written Opinion dated Jan. 2, 2012.

Kim, Y.H., et al., "Preparation and characterization of the Antibacterial Cu Nanoparticle Formed on the Surface of SiO2 Nanoparticles," J. Phys. Chem B 2006, vol. 110, pp. 24923-24928.

Barik, T.K., et al., "Nanosilica-From MEdicine to Pest Control," Parasitol, R es 2008, vol. 103, pp. 253-258.

Cho. et al.. "The Study of Antimicrobial Activity and Preservative Effects of Nanosilver Ingredient". Electrochimica Acta 51,956-960 (2005).

Feng, et al. "A Mechanistic Study of the Antibacterial Effect of Silver Ions on *Escherichia coli* and *Staphylococcus aureus*", Journal of Biomedical Materials Research 52, 662-668 (2000).

Jasiorski, et al., "Textile with silver Silica Spheres: its Antimicrobial Activity against *Escherichia coli* and *Staphylococcus aureus*", Journal of Sol-Gel Science and Technology 51, 330-334 (2009).

Lu, et al., "A Simple and Effective Route for the Synthesis of Crystalline Silver Nanrods and Nanowires", Advanced Functional Materials 14, 183-189 (2004).

Solomon, et al. (2007). "Synthesis and study of silver nanoparticles." Journal of Chemical Education. 84, 322-325.

Pal, et al. (2007). "Does the antibacterial activity of silver nanoparticles depend on the shape of the nanoparticle? A study of the gram-negative bacterium *Escherichia coli*." Applied Environmental Microbiology 73, 1712-1720.

Jung, et al. (2008). Antibacterial activity and mechanism of action of the silver ion in *Staphylococcus aureus* and *Escherichia coli*. Applied Environmental Microbiology 74, 2171-2178.

Frisken, B. J. (2001 ). "Revisiting the method of cumulants for the analysis of dynamic light-scattering data." Applied Optics 40, 4087-4091.

Schillinger, et al. (1989). "Antibacterial Activity of Lactobacillus-Sake Isolated from Meal." Applied and Environmental Microbiology 55, 1901-1906.

Rastogi, et al., "Ag colloids and Ag clusters over EDAPTMS-coated silica nanoparticles:synthesis, characterization, and antibacterial activity against *Escherichia coli*." Nanomedicine-Nanotechnology Biology and Medicine 7, 305-314 (2011 ).

Collins, T.J., "ImageJ for Microscopy Biotechniques." 43, 25-30(2007).

Naik, et al., "Biomimetic synthesis and patterning of silver nanoparticles." Nature Materials 1, 169-172 (2002).

Mock, et al., "Shape effects in plasmon resonance of individual colloidal silver nanoparticles." Journal of Chemical Physics 116, 6755-6759 (2002).

Office Action issued in Indian Application No. 2375/KOLNP/2011 dated May 4, 2017 (10 pages).

International Search Report issued in International Patent Application No. PCT/US2009/006496, dated Apr. 30, 2010 (4 pages).

\* cited by examiner

Fig. 6a
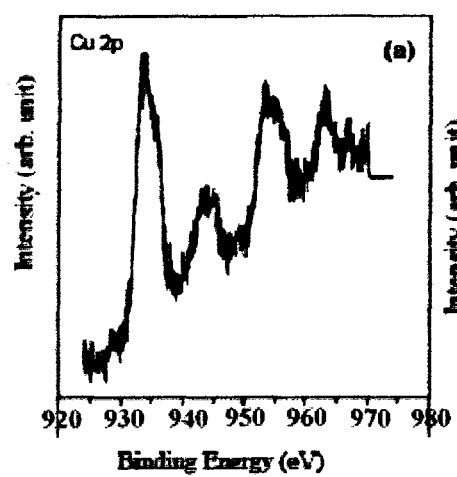
Fig. 6b
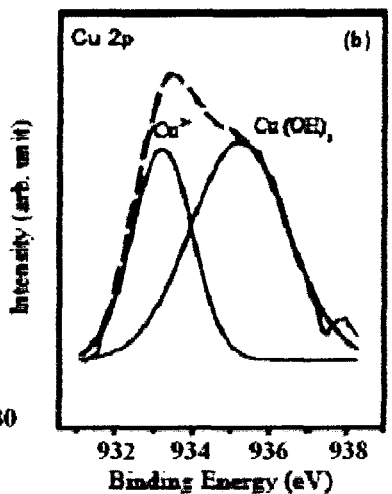
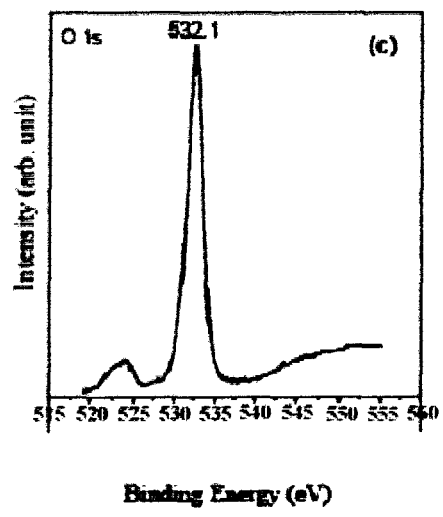
Fig. 6c
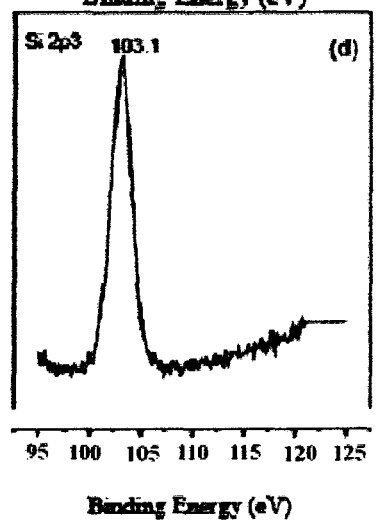
Fig. 6d

SILICA-BASED ANTIBACTERIAL AND ANTIFUNGAL NANOFORMULATION

CROSS-REFERENCE TO RELATED APPLICATIONS

This application is a Divisional of copending U.S. patent application entitled "Silica-Based Antibacterial and Antifungal Nanoformulation" filed on Jun. 20, 2012 and assigned Ser. No. 13/527,691, which is a Divisional of copending U.S. patent application entitled "Silica-Based Antibacterial and Antifungal Nanoformulation", filed on Dec. 10, 2008 and assigned Ser. No. 12/332,021, which is incorporated by reference in its entirety.

This invention relates to silica-based nanoformulations, and in particular to, compositions and methods for fabricating silica-based nanoparticles and silica-based nanogels, or a combination thereof, that provide a unique nanoenvironment to host antibacterial and antifungal agents, method of synthesis and use. The research herein was supported in part by the National Science Foundation (NSF Grant 0651976 and NSF-NIRT Grant 0506560).

BACKGROUND AND PRIOR ART

Global Concern

The globalization of business, travel and communication brings increased attention to worldwide exchanges between communities and countries, including the potential globalization of the bacterial and pathogenic ecosystem. Bactericides and fungicides have been developed to control diseases in man, animal and plants, and must evolve to remain effective as more and more antibiotic, pesticide and insecticide resistant bacteria and fungi appear around the globe.

Bacterial resistance to antimicrobial agents has also emerged, throughout the world, as one of the major threats to both man and the agrarian lifestyle. Resistance to antibacterial and antifungal agents has emerged as an agricultural issue that requires attention and improvements in the treatment materials in use today.

For example, focusing on plants, there are over 300,000 diseases that afflict plants worldwide, resulting in billions of dollars of annual crop losses. In 1990, over 7.3 billion dollars were spent in the United States on pesticide products.

Antibacterial and antifungal (Anti-B/F) agents include, but are not limited to, metallic copper (Cu), copper salts, copper complexes, metallic zinc (Zn), zinc oxides, zinc salts, metallic silver (Ag), silver salts, silver complexes, titanium dioxide ($TiO_2$), cerium oxides, magnesium oxides, zirconium oxides, polyethyleneimine (PEI), carbon, mixed carbon or soot, fullerenes, carbon nanotubes and the like. The preceding compounds are only a few examples of antibacterial and antifungal agents used by man in a quest to control or eliminate infectious diseases in our global environment.

The antibacterial/antifungal (Anti-B/F) formulations in existence today could be improved and made more effective if the following features were included in the formulation. For example, a desirable formulation would have an increased, uniform distribution on a treated surface area, improved adherence to treated surface, a means for controlling and sustaining the release of the active ingredients, and dosage levels that avoid any toxic impact on the environment and/or the treated surface.

The present invention provides a composition that hosts antibacterial/antifungal formulations and together, the host composition and antibacterial/antifungal ingredients provide functional benefits that solve many problems and overcome many limitations in the prior art.

A synthesis method for preparation of a silica matrix with embedded metallic particles is reported in U.S. Pat. No. 6,548,264 to Tan et al., U.S. Pat. No. 6,924,116 to Tan et al., and U.S. Pat. No. 7,332,351 to Tan et al., which are incorporated herein by reference.

Use of Copper (Cu) Fungicides/Bactericides

In modern agriculture, copper (Cu) compounds are widely used as fungicides/bactericides. Cu compounds, in relatively low concentration, are quite toxic to thalophyte organisms, such as, fungi, bacteria, and algae. This property of toxicity has been utilized for over 100 years for control of fungal and bacterial diseases of plants. In 1761, it was discovered that seed grains soaked in a weak solution of Cu sulfate inhibited seed-borne fungi.

The greatest breakthrough for Cu salts undoubtedly came when the French scientist Millardet announced to the world in 1885 that he had found a cure for the dreaded mildew using mixtures of Cu sulfate, lime and water (known as Bordeaux mixture). Cu based fungicides/bactericides are used worldwide because Cu compounds are relatively safe; development of resistance by plant pathogens has been minimal; in demand by developing third world countries and the increasing requirements for food requiring more efficient agriculture; and an increase in government regulations and restrictions or outright banning of alternative products due to their toxicological and environmental impact requires safe treatment formulations, as discussed by H. W. Richardson in *Handbook of Copper Compounds and Applications*, "Copper fongicides/bactericides" H. W. Richardson, Editor, 1997, Marcel Dekker, Inc.: New York, N.Y., pages 93-122.

The toxicity of Cu is largely due to its tendency to alternate between its cuprous, Cu(I), and cupric, Cu(II), oxidation states. Under aerobic conditions, this redox cycling leads to the generation of highly reactive hydroxyl radicals that readily and efficiently damage biomolecules, such as DNA, proteins, and lipids. The underlying Fenton-like reactions involving reactive oxygen species can be described as Cu-catalyzed Haber-Weiss reactions. While the reaction of dihydrogen peroxide with superoxide primarily has a negligible rate constant as shown below in equation 1, this rate is greatly accelerated in the presence of Cu.

$$H_2O_2 + O_2^- \rightarrow O_2 + OH^- + OH^* \qquad (1)$$

Cu ions are believed to catalyze this reaction as shown in equations 2 and 3.

Cu(II) is initially reduced by superoxide as shown in equation 2, $$Cu(II) + O_2^- \rightarrow Cu(I) + O_2 \qquad (2)$$

followed by reoxidation by dihydrogen peroxide as shown in equation 3, $$Cu(I) + H_2O_2 \rightarrow Cu(II) + O_2 + OH^- + OH^* \qquad (3)$$

resulting in a net production of the hydroxyl radical.

Most fungicides and bactericides do little to kill an established infection of fungi and bacteria, respectively, but act by protecting the host from the possibility of infection. If the protectant is applied after the onset of disease symptoms, control will often be minimal. Similarly, Cu compounds inhibit germination of the fungal spore or bacterial cell, the primary "seeds" responsible for dissemination and reproduction of the fungus or bacterium. Because the spore or cell removed from the current infection cycle does not mature nor reproduce in the presence of Cu, the fungus or bacterium are effectively killed.

The fungicidal/bactericidal value is a measure of the toxicity of a material to the pathogen and is usually expressed as an LD5o, primarily a laboratory based in vitro toxicity measurement, wherein LD stands for Lethal Dose and $LD_{50}$ is the amount of material or dose which causes the death of 50% of the target population.

The protective value is a measure of the ability of a material to protect the host organism, for example, a plant, from infection, which is primarily a measurement under field conditions. For example, Cu sulfate has an excellent ability to inhibit fungal spore or bacterial cell germination in the laboratory; however, in the field it exhibits no persistence, because of its solubility. It has limited protective value because it is quickly removed from the plant surface at the first rain. Furthermore, Cu sulfate may produce sufficient soluble Cu to be toxic to the plant (phytotoxic). A Cu compound must be chosen that is relatively resistant to weathering and supplies enough Cu to be toxic to the fungal spores and bacterial cells without adversely affecting the plant.

An important consideration is whether to use "soluble" or "insoluble" copper (Cu) for long-term fungicidal or bactericidal protection. The "soluble" Cu refers to Cu based salts (such as Cu sulfate) that hydrolyze completely in water, producing ionic Cu. The "insoluble" (sparingly soluble) Cu compounds act as a reservoir from which Cu ion is released to the plant surface on which it is deposited upon application.

Solubilization of Cu in the field application is governed by several interrelated factors, such as, the total soluble Cu that is dependent on gross factors such as dosage/residue and the amount at any locus is dependent on distribution. In addition, the limiting concentration of soluble Cu will be dictated by the thermodynamic tendencies of the Cu compound to solubilize in the surrounding media and the concentration of soluble Cu at any given time will be further dependent on the rates at which solubilization occurs, for example, the velocity response of the system toward equilibrium. All of these factors are complicated by the system dynamics. The total dosage/residue decreases over time due to weathering and redistribution of the remaining residue occurs. Particles are exposed to constantly varying moisture and exudate levels, and the system is constantly in a state of flux, moving toward equilibrium. Therefore, the system must be kinetically responsive if toxic doses of Cu are to be maintained. For long-term protection, "insoluble" Cu appears to be preferred in field applications.

Thus, certain properties must be optimized if copper (Cu) fungicides/bactericides are to demonstrate effective protective ability. A dosage must be chosen which is adequate to defend against infection. The deposition of the Cu particles on the plant surface must occur and they must adhere to and/or be retained by the surface. The properties of the adherence by the Cu particle and the retention by the plant surface are determining factors of the tenacity, or overall ability of the Cu compound to persist on the plant surface. Factors such as wind, rain, and leaf movements will all cause erosion of the Cu particle deposits by physical and mechanical means. Rain, mist, and dew will also give rise to the chemical dissolution of those deposits. All of these factors are important in the establishment and maintenance of sufficient coverage to protect plants from pathogens.

The limiting quantity and nature of soluble Cu species at equilibrium with the surrounding media is governed by the absolute solubility of the Cu compound in water and the nature and concentration of the complexing agents present in the media. The quantity of dissolved Cu at any given time is also determined by the rate at which the equilibrium can be established. Equilibrium conditions are determined by the system thermodynamics. The rate at which equilibrium is established is dictated by the kinetic responsiveness of the system. It should be emphasized that thermodynamic considerations allow the identification of the position of the system relative to equilibrium. Further, there will be a tendency to move toward the equilibrium. Understanding of these factors is crucial for developing a new generation of Cu based fungicides/bactericides with sustained ionic Cu release mechanism.

Estimation of the world market for fungicides and bactericides by type of Cu compound and year of introduction is shown in Table 1 below (data published in 1988, Source: H. W. Richardson, *Handbook of Copper Compounds and Applications*. supra).

TABLE 1

Estimation of World Market for Fungicides/Bactericides by Type of Cu Compound

| Cu Compound | Quantity (Tons/Yr) | % of Market | Year Introduced |
|---|---|---|---|
| Cu(II) oxychloride | 71,000 | 51.1 | 1990 |
| Cu(II) sulfate | 48,000 | 34.6 | 1761 |
| Cu(II) sulfate + lime (Bordeaux mixture) | | | 1873 |
| Cu(II) sulfate + soda ash (Burgundy mixture) | | | |
| Basic Cu(II) sulfate | | | |
| Cu(I) oxide | 6,000 | 4.3 | 1932 |
| Cu(II) kydroxide | 11,000 | 7.9 | 1960 |
| Others: Cu(II)ammonia complex., $CO_3$ and $PO_4$ | | | 1917 |

It is clear that Cu based fungicides/bactericides have been applied for a long-time and have high societal and economic impact in agriculture, water treatment and domestic living. There are approximately 2,000 registered products which contain copper compounds as active ingredients.

Several Cu compounds are registered in the United States for management of over 100 diseases on almost 50 food crops. The Cu compounds exhibit varying degrees of effectiveness for any target organism on any given host. The most common forms of Cu that satisfy these conditions to varying degrees are the normal hydrolysis products of Cu(I) and Cu(II) salts (also known as "insoluble Cu" of "fixed Cu" compounds): Cu(I) oxide (Cu20), Cu(II) oxychloride (CuCh. 3Cu(OH)2), tribasic Cu(II) sulfate (CuS04. 3Cu (OH)2, and Cu hydroxide (Cu(OH)2). In the past most Cu products were wettable powders and contained around 50% Cu (active ingredient). However today's formulations contain from 8% to 75% Cu and application rates varying accordingly. Products are formulated as wettable powders, wettable granules, liquid flowable suspensions and aqueous liquids.

By the mid-1930s, Bordeaux mixture was largely replaced by basic Cu(II) sulfate, Cu(I) oxide, Cu(II) oxychloride. These Cu compounds are easy to handle and relatively less phytotoxic in comparison to the Bordeaux mixture. Cu hydroxide was introduced in 1960. Kocide® 3000 is the latest Cu hydroxide based product from the DuPont Company, Wilmington, Del., which is one of the most popular fungicides/bactericides.

Currently used Cu compounds possess unique set of physical and chemical properties. They differ in their total amount of metallic Cu content and aqueous solubility. It is well understood that the antibacterial activity will depend upon the availability of soluble ("free and reactive") Cu ions in the formulation. Among the existing Cu compounds, tribasic Cu sulphates and cuprous oxide are least soluble, whereas Cu hydroxides are more soluble than Cu oxychloride.

Again, too much Cu will cause phytotoxicity and adversely affect the environment whereas sparingly soluble Cu compounds will be less effective, requiring multiple applications, thus labor extensive. A robust Cu formulation must meet at least the following three criteria: (i) the Cu release rate must be maintained at a optimum level (sustained release mechanism while minimizing phytotoxicity) to provide long-term protection against pathogen, (ii) the Cu compound must stick well to the plant surface to withstand wind blown rain so that multiple applications will not be required and (iii) the Cu compound will not cause toxicity to the environment (i.e. environmentally-safe). Due to inherent chemical and physical properties, however, the existing Cu compounds are seriously limited to meet these criteria.

With regard to copper (Cu) compounds, the efficacy of a Cu compounds can be considerably improved by reducing the particle size according to Torgeson, D. C., ed. *Fungicides—An Advanced Treatise*, Agricultural and Industrial Applications and Environmental Interaction. Vol. 1. (1967), Academic Press: New York, N.Y., page 697. The smaller the particle size the greater is the number of particles per gram and therefore the greater the fungicidal or bacterial activity. This welcomes nanoscience and nanotechnology that deals with matters in the nanoscale dimension, typically 1-100 nanometer range.

Navarro, E., et al., in "*Environmental behavior and ecotoxicity of engineered* 5 nanoparticles to algae, plants, and fungi," *Ecotoxicology*, 2008. 17(5): pages 372-386 teaches that specific surface area as shown in FIG. 1a increases exponentially as the particle size decreases below 100 nanometers. Likewise, Oberdorster, G. et al, in *Nanotoxicology: An Emerging Discipline Evolving from Studies of Ultrafine Particles*. Environmental Health Perspectives, 2005. 113(7): pages 823-839 teaches that the percentage of surface atoms exponentially increase as the particle size decreases below 100 nm as shown in FIG. 1b. Thus, with smaller particles coverage is improved and there is significantly more surface area available per gram of product to release Cu ions when moisture is present.

Smaller particles also resist dislodgement better as they are lighter and have a larger surface area relative to their weight; hence a greater area of contact with the plant surface, and the result is an increase in the total force of adhesion. Cu formulations with smaller particles will therefore produce improvements in disease control through better coverage, rain-fastness, and longevity of the product and release of Cu ions on the plant surface. In this regard, some improvements in the product quality have been made on Cu compounds over the past decade. To date, however, no major breakthrough has been made that could be considered revolutionary. This strongly demands development of a new generation of Cu based fungicides/bactericides that will meet the above-mentioned criteria.

Inhibiting Growth o(Mold and Mildew

Growth of fungus, such as, mold and mildew fungi is a serious problem in warm, moist environments, such as in tropical climates. In the presence of nutrients which are found abundantly in house/building materials such as dry walls, wood, grout, carpet backing and the like, mold and mildew thrives.

Mold and mildew have similar characteristics, but are different types of microscopic fungi and are often different in color and texture and can be seen growing on objects both inside and outside buildings. Mold and mildew growth is not only detrimental to health but also presents an unsightly appearance when colonies are established on interior or exterior surfaces of buildings. Mildew is more often found in bathroom showers, tubs, ceramic tile grout, paper and fabric; mold is usually found in foods. They can be difficult to tell apart as they both use spores for reproduction. Mold is often black, green, red or blue in color, while mildew is usually gray or white. Musty and moldy odors are produced by chemical changes taking place during the mold life process and are scientifically designated as microbial Volatile Organic Compounds (mVOCs) Waste products are given off by actively growing molds.

Airborne mold spores can seriously compromise indoor air quality and cause severe allergy, asthma and other immunological problems. Health effects such as headaches, dizziness, nausea and coughing have been linked to exposure to mVOCs. Irritation of the eyes and throat may also occur as a result of breathing mold toxins. Moldy food should not be eaten. A mildew infestation on paper and some fabrics cannot be scrubbed off, but a mildew remover can usually get rid of mildew on harder surfaces, such as, surfaces in bathrooms, kitchens and on exterior walls.

Mold spores are resistant to high temperature, UV light and desiccation. The spores are abundant in the environment and remain dormant in unfavorable conditions and germinate rapidly in a favorable environment (warmth, moisture and nutrients). Bleach solutions are effective in killing both mold and mildew and are considered a very effective treatment world-wide. However, the action of bleach does not last long; multiple applications are required within one or two weeks.

U.S. Pat. No. 3,992,146 to Fazzalari describes a process using biocidal solutions containing copper sulfate and a surfactant to inhibit growth of fungi on hard porous surfaces, such as grout.

It is desirable to use nanotechnology to expand the use of copper (Cu) loaded silica nanoparticle/nanogel formulations with superior antibacterial activity for treating areas that favor and foster the growth of mold and mildew; in addition, it is desirable for a single treatment to remain effective for from at least two to six months because of the release of ionic Cu in a slow, sustained manner and in quantities that would not violate the EPA Water Quality Standard Rule issued on Dec. 1, 1992, setting water quality standards for copper as a priority toxic pollutant.

Treatment o(Diseases in Plants

The state of the art for methods and treatment of diseases in plants, and specifically canker in citrus plants is found in a representative sample of patents listed below:

U.S. Pat. No. 3,983,214 to Misato et al teaches fungicidal compositions and method for protecting plants by the use of compositions which contain organic acids as an active ingredient, alkali metal salts of these organic acids, ferric citrate, ferric lactate, glycerine, aluminum chloride and esters formed between sugar and higher fatty acids having 8 to 18 carbon atoms. The compositions have no phytotoxicity and no mammalian toxicity and present no risk of pollution of soil.

U.S. Pat. No. 5,462,738 to LeFiles et al. discloses a granular copper hydroxide dry flowable bactericide/fungicide with improved biological activity and a method of making and using.

U.S. Pat. No. 5,939,357 to Jones et al. provides a fungicide composition which has a bicarbonate-containing inorganic salt ingredient which enhances the efficacy of a fungicide ingredient for treatment of cultivated crops.

U.S. Pat. No. 6,471,976 to Taylor et al. discloses an improved copper complex bactericide/fungicide containing a partially neutralized polycarboxylic acid and a method of making and using.

U.S. Pat. No. 7,163,709 to Cook et al. discloses a composition and method of providing ionic forms or compounds of any combination of three metals (copper, gold and silver) to produce a product that can be used as an antimicrobial agent, hard surface disinfectant, foliar spray or water treatment. The composition is aerosolized, misted, vaporized, fogged, humidified to produce micronized particles which are able to remain in suspension in the air for long periods of time to act on air-borne fungal spores and/or pathogens. This would be an enormously expensive composition.

U.S. Pat. No. 7,226,610 to Winniczuk teaches compositions and methods for the treatment and prevention of disease in plants, especially citrus canker, using composition including various combinations of d-limonene, wax and monohydric alcohol.

U.S. Patent Publ. No. U.S. 200110051174 to Staats provides an antimicrobial composition containing quaternary ammonium compounds, a surfactant, a wetting agent, a drying agent, a hydrophilic film forming agent, a hydrophobic water proofing agent and water, having antiviral, antibacterial, and antifungal properties, applied to plants and trees by spray coating and/or through systemic delivery to protect against harmful and destructive organisms.

U.S. Patent Publ. No. US 2007/0087023 and U.S. Patent Publ. No. US 2007/0098806 both to Ismail et al disclose a polymer-based antimicrobial agent that includes a water-soluble polymer and oligodynamic metal ions (e.g., nano-sized silver particles) that interact with the water-soluble polymer to treat or prevent citrus canker.

Thus, there is a wide array of fungicidal/bactericidal compositions represented in the patent literature with formulations that include, acids, polymeric compounds, metallic ions, undesirable components such as surfactants or oils. Cost, effectiveness and bacterial or fungal resistance to treatment are also considerations.

With regard to citrus canker, a particularly acute and critical situation has developed in the United States. Citrus canker is a bacterial disease of citrus that causes premature leaf and fruit drop. Symptoms of the disease are exhibited on leaves and fruit by brown, raised lesions surrounded by an oily, water-soaked margin and a yellow ring or halo. Old lesions in leaves may fall out, creating a shot-hole effect.

Citrus canker does not harm humans or animals or plant life other than citrus. However, citrus canker affects all types of citrus, including oranges, sour oranges, grapefruit, tangerines, lemons and limes. Canker causes the citrus tree to continually decline in health and fruit production. Ultimately, the tree will produce no fruit at all.

Citrus canker is highly contagious and can be spread rapidly by windborne rain, lawnmowers and other landscaping equipment, people carrying the infection on their hands, clothing, or equipment, moving infected or exposed plants or plant parts.

The United States Department of Agriculture (USDA) withdrew eradication program funding due to the impacts of legal constraints and the 2004/2005 hurricanes that caused canker to spread so far that eradication was no longer possible.

Florida is currently under a statewide quarantine by the USDA and no citrus may leave the state unless the USDA has issued a limited permit. No Florida grown citrus may enter any citrus producing states or territories. No citrus plants or parts may enter or exit Florida.

Over 16 million trees have been destroyed in Florida since canker was first identified in Florida in 1910. Twice the state of Florida has declared that canker was eradicated, in 1933 and again in 1994, only to have the canker disease resurface a third-time in 1995 near Miami International Airport. In 2008, the citrus industry in Florida is now quarantined because of canker disease that was spread by the 2004/2005 hurricanes. Once productive groves, land and trees are becoming unproductive at an enormous cost to the state and its citizens.

There remains a continuing need for the development of new and more effective fungicides/bactericides that are inexpensive and easy to manufacture which possess preventive, curative and systemic activity for the protection of not only citrus trees, but all cultivated plants, with a minimum of phytotoxic side effects. The present invention uses nanotechnology to meet the need for an inexpensive, more effective fungicide/bactericide.

SUMMARY OF THE INVENTION

A first objective of the present invention is to provide a composition and method for fabricating a silica-based nanoformulation that provides a unique nanoenvironment to host antibacterial and antifungal agents.

A second objective of the present invention is to provide a silica-based nanoformulation that provides a unique nanoenvironment to host antibacterial and antifungal agents with controlled release kinetics, establishing a sustained release mechanism.

A third objective of the present invention is to provide a silica-based nanoformulation that provides a unique nanoenvironment to host antibacterial and antifungal agents (Anti-B/F) to enhance the efficacy of the Anti-B/F agents.

A fourth objective of the present invention is to provide a nanoformulation consisting of silica nanoparticle (SiNP), or silica nanogel (SiNG) or a combination of SiNP and SiNG.

A fifth objective of the present invention is to provide a simple, cost-effective fabrication or synthesis method for a silica-based nanoformulation with antibacterial and antifungal content that can be prepared on-site, in a few hours, in a single-pot synthesis method, requiring no purification steps.

A sixth objective of the present invention is to provide a simple, cost-effective fabrication or synthesis method for a concentrated silica-based nanoformulation with antibacterial and antifungal content that can be prepared on-site, diluted for field application by a non-technical person.

A seventh objective of the present invention is to provide a silica-based nanoformulation with antibacterial and antifungal content for treating a citrus canker disease-prone surface by providing uniform coverage to that surface, surface adherence for a satisfactory period of time, sustained release over time, better control of Anti-B/F release, a reduction in toxicity and stress to the environment in the treated area.

An eighth objective of the present invention is to provide a silica-based nanoformulation with antibacterial and antifungal content for treating a citrus canker disease-prone surface with a broad array of benefits, including, but not limited to, surface adherence for a satisfactory period of time, sustained release over time, control of Anti-B/F release, reduced toxicity and stress to the environment in the treated area.

A ninth objective of the present invention is to provide a silica-based nanoformulation with antibacterial and antifungal content for treating citrus canker and preventing canker disease for a period of from five to nine months.

A tenth objective of the present invention is to provide a silica-based nanoformulation with antibacterial and antifungal content for the agriculture industry (vegetables, flowers, grass and other plants), household applications (fabrics, leather, plastics, paint and the like).

An eleventh objective of the present invention is to provide a copper (Cu) loaded, silica-based nanoformulation with residual fertiziling properties for soil wherein leaves and branches of plants treated with the nanoformulation continue to release Cu nutrients when the leaves and branches drop to the ground.

A twelfth objective of the present invention is to provide a copper (Cu) loaded, silica-based nanoformulation with residual fertiziling properties for soil wherein when plants and trees treated with the nanoformulation herein are harvested for mulch or compost, the soil is enriched with residual Cu ions.

Another objective of the present invention is to provide a copper (Cu) loaded, silica-based nanoformulation with superior antifungal properties to inhibit the growth of mold and mildew for at least six months by the release of a fungicide in a slow and sustained manner.

A preferred method for synthesizing a silica-based nanoformulation containing antibacterial and antifungal agents using a one-pot, acid-catalyzed, sol-gel process, includes selecting a reaction vessel containing an acidic reaction medium, adding tetraethoxysilane (TEOS), water, ethanol and an antibacterial or antifungal agent containing copper ions to the reaction vessel with the acidic medium to form mixture I, allowing the reaction of mixture I to continue for approximately one hour to facilitate the formation of a plurality of silica-based nanoparticles, adding a neutralizing agent after the formation of a plurality of nanoparticles to adjust the pH value of the reaction mixture to approximately 7.0, allowing the neutralized reaction of mixture I to continue for approximately 12 hours, preferably overnight, to allow gelation to occur, wherein the nanogel structure consists of interconnected nanoparticles; and collecting a porous silica-based nanogel having antibacterial and antifungal agents bound in a plurality of interconnected nanoparticles of the nanogel.

The preferred acidic reaction medium of the method is an aqueous solution of an acid selected from one of hydrochloric acid, sulfuric acid and nitric acid. The preferred antibacterial or antifungal agent is a plurality of copper (Cu) ions sourced from a copper compound.

It is also preferred that the reaction of mixture I occur at ambient temperatures and pressures.

It is preferred that the plurality of interconnected nanoparticles of the nanogel contain a plurality of Cu ions electrostatically bound to the nanoparticle core, a plurality of Cu ions covalently bound to a hydrated shell surface and nanopores of the nanoparticle, and a plurality of Cu oxide/hydroxide as nanoclusters/nanoparticles bound to the surface of the nanoparticle.

A preferred composition and method for treating and preventing disease in a plant species consists of a silica-based nanoformulation, preferably containing a plurality of copper ions embedded in a plurality of silica nanoparticles and more preferably, a plurality of copper ions embedded in a silica nanogel. Preferably the plurality of copper ions is from copper compounds, such as, metallic copper, copper oxide, copper oxychloride, copper sulfate, copper hydroxide and mixtures thereof.

Preferably the diseased plant treated by the preferred composition is a member of the citrus species, wherein the disease is citrus canker caused by any species of Xanthomonas.

It is preferred that during treatment, the plurality of copper (Cu) ions is released in a 15 sustained manner for long-term treatment of the plant for a time period of at least six months.

A preferred method for treating or preventing disease in a plant species comprising applying to the plant species a composition that comprises a silica-based nanoformulation, wherein the preferred composition further comprises a plurality of copper ions embedded in a plurality of silica nanoparticles, more preferably, a plurality of copper ions embedded in a silica nanogel.

The composition further includes a plurality of copper ions from copper compounds, such as, metallic copper, copper oxide, copper oxychloride, copper sulfate, copper hydroxide and mixtures thereof.

A preferred method for treating and inhibiting the growth of mold and mildew on a surface selected from the group consisting of interior and exterior walls of buildings, ceilings, ceramic tile grout, and bathroom fixtures comprising applying to the surface, a composition that comprises a silica-based nanoformulation. The preferred silica-based nanoformulation is a plurality of interconnected nanoparticles of the nanogel contain a plurality of Cu ions electrostatically bound to the nanoparticle core, a plurality of Cu ions covalently bound to a hydrated shell surface and nanopores of the nanoparticle, and a plurality of Cu oxide/hydroxide as nanoclusters/nanoparticles bound to the surface of the nanoparticle.

The preferred source of the plurality of Cu ions is selected from metallic copper, copper oxide, copper oxychloride, copper sulfate, copper hydroxide and mixtures thereof.

A preferred method for adding nutrients to the soil includes treating vegetation with a copper (Cu) loaded silica nanoparticle formulation, allowing leaves and branches to drop to the ground, and leaving the treated leaves and branches to biodegrade and thereby fertilizing the soil with Cu ion nutrients in a slow-release, non phytotoxic manner.

Another preferred method for adding nutrients to soil includes treating vegetation with a copper (Cu) loaded silica nanoparticle formulation, harvesting and comminuting the vegetation to form mulch or compost, and spreading the mulch or compost over the soil to allow the leaching of Cu ion nutrients in a slow-release, non-phytotoxic manner with exposure to atmospheric conditions selected from at least one of rain, wind, snow, and sunlight.

Further objects and advantages of this invention will be apparent from the following detailed description of a presently preferred embodiment that is illustrated schematically in the accompanying drawings.

BRIEF DESCRIPTION OF THE FIGURES

FIG. 1*a* is a graph showing the exponential increase of surface molecules as a function of decreasing particle size. (Prior Art)

FIG. 1*b* is a graph of the relationship between specific surface area of a spherical particle and the size of the particle (diameter in nm). (Prior Art)

FIG. 2 is a schematic representation of the silica-based nanoformulation of the present invention showing a copper (Cu) silica nanoparticle (CuSiNP).

(EDTA) forming a water-soluble Cu-EDTA complex.

Figures 4A, 4B, 4C, 4D:
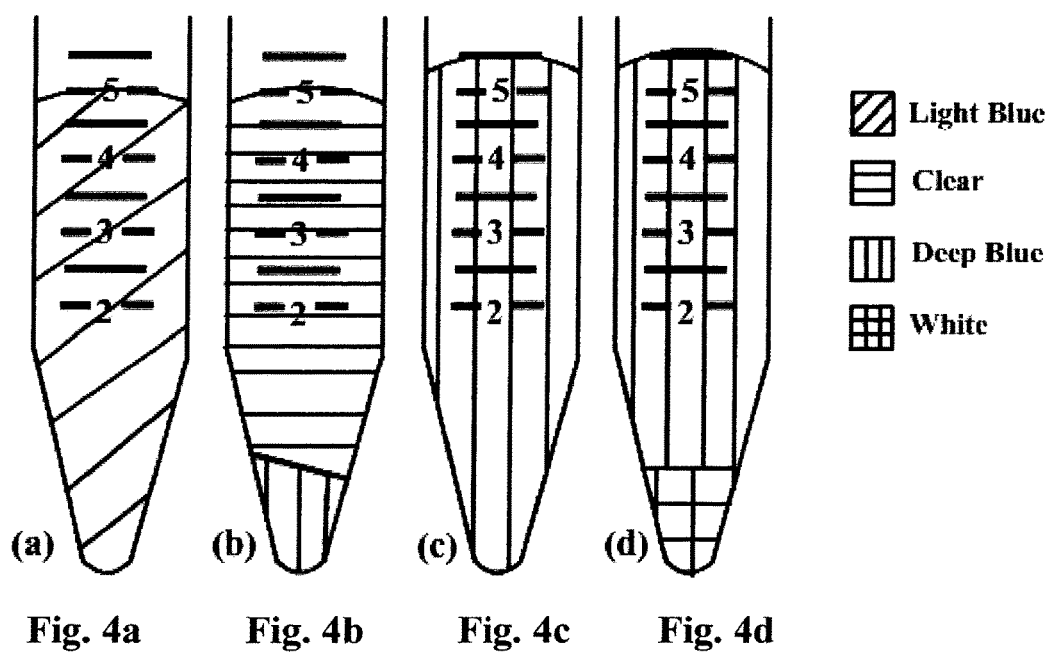
FIG. 4*a* shows the binding of copper (Cu) to silica nanogel (SiNG).

FIG. 4*b* shows the water dispersible CuSiNG after centrifugation with the separation of residue from the supernatant liquid.

FIG. 4*c* shows a water-soluble CuSiNG mixture treated with ethylenediamine tetraacetic acid.

FIG. 4*d* shows the water-soluble Cu-EDTA complex after centrifugation with the separation. of the Cu-EDTA complex and a residue of silica nanogel (SiNG).

Figure 5:
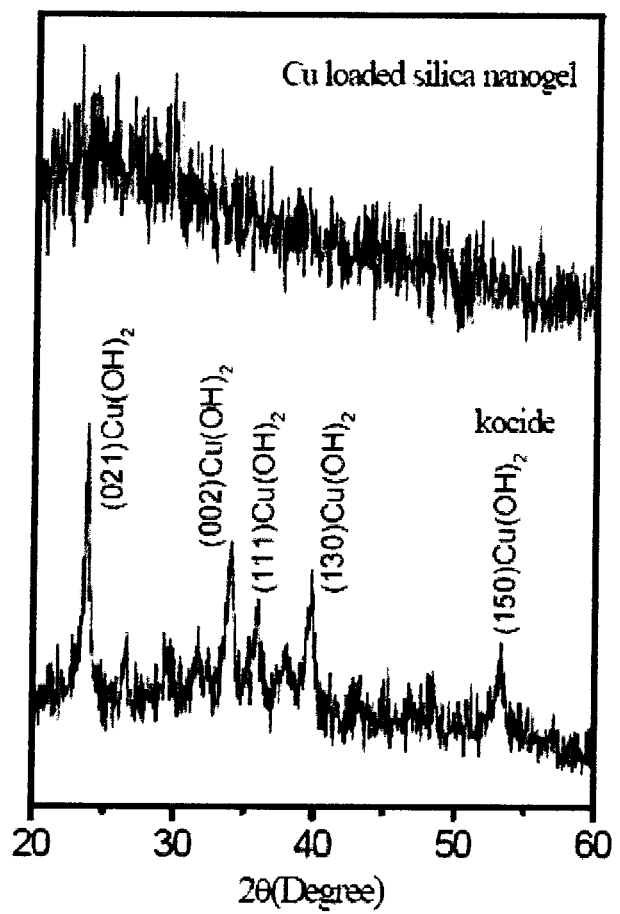

FIG. 5 is an X-ray Diffraction (XRD) pattern of a CuSiNG sample and a commercially available bactericide/fungicide, DuPont™ Kocide® 3000.

FIG. 6*a* is the X-ray photoelectron spectroscopy (XPS) spectrum for Cu in a CuSiNG sample.

FIG. 6*b* is the X-ray photoelectron spectroscopy (XPS) spectrum for Cu in the core of a CuSiNG sample.

FIG. 6*c* is the X-ray photoelectron spectroscopy (XPS) spectrum for oxygen (0) in a CuSiNG sample.

FIG. 6*d* is the X-ray photoelectron spectroscopy (XPS) spectrum for silicon (Si) in a CuSiNG sample.

Figure 7A:
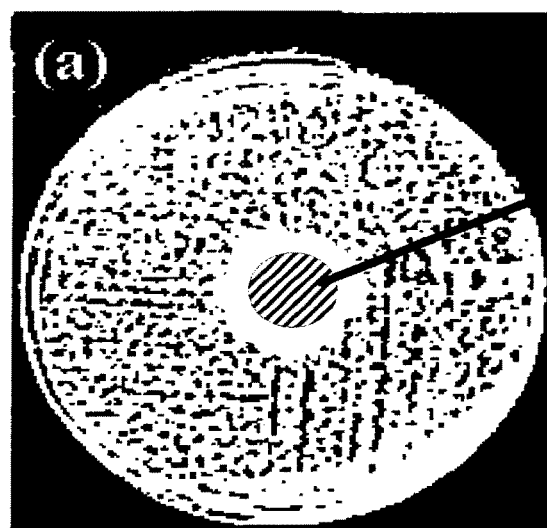

FIG. 7*a* is a drawing of a disk diffusion assay of CuSiNG having a pH of approximately 7.

Figure 7B:
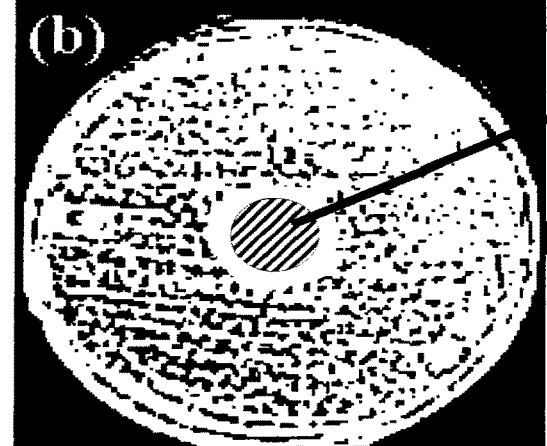

FIG. 7*b* is a drawing of a disk diffusion assay of copper sulfate (CuS04) having a pH of approximately 7.

Figure 7C:
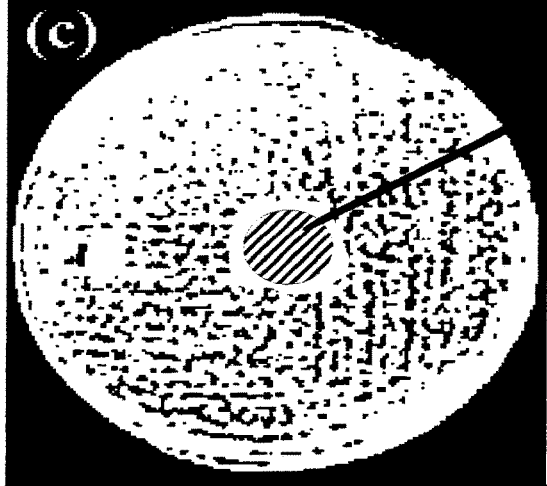

FIG. 7*c* is a drawing of a disk diffusion assay of DuPont™ Kocide® 3000 fungicide/bactericide.

Figure 8:
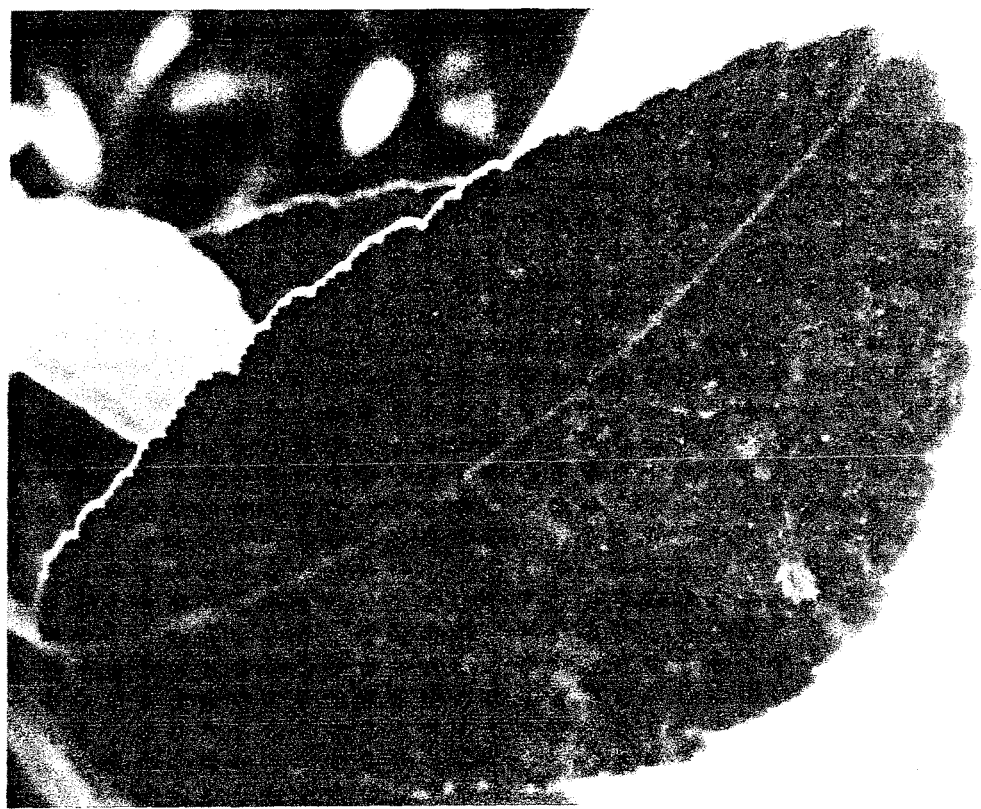

FIG. 8 is a digital image of a lemon tree leaf taken 5 days after the initial application of a silica-based nanoformulation of the present invention (CuSiNG) is exposed to heavy rain, wind and thunderstorm conditions in an outdoor environment.

Figures 9A, 9B, 9C, 9D:
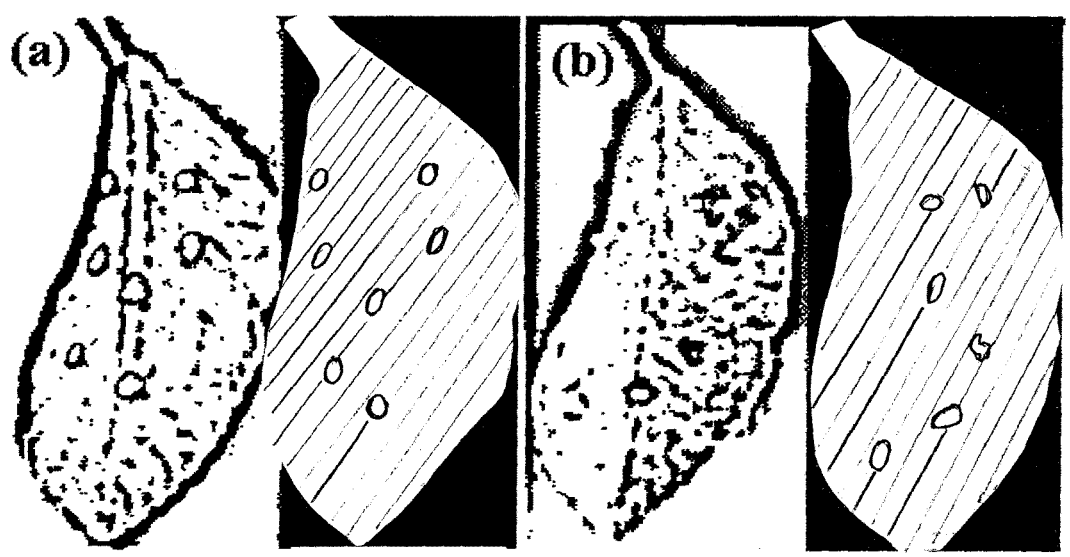

FIG. 9*a* shows digital field image of CuSiNG on the leaf surface before rain water is sprayed on the leaf surface.

FIG. 9*b* is a drawing of the fluorescent image of the leaf in FIG. 9*a* showing adherence of CuSiNG before rain water is sprayed on the leaf surface.

FIG. 9*c* shows a digital field image of CuSiNG on the leaf surface after approximately 5 minutes of continuous rain water spray onto the leaf surface.

FIG. 9*d* is a drawing of the fluorescent image of the leaf in FIG. 9*c* showing adherence of CuSiNG after approximately 5 minutes of continuous rain water spray onto the leaf surface.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation. It would be useful to discuss the meanings of some words and abbreviations used herein to explain the invention in greater detail.

CuSiNG stands for Copper Silica NanoGel

CuSiNP stands for Copper Silica NanoParticle

NG stands for Nanogel, which is the gel-like substance formed by the interconnection of nanoparticles.

NP stands for Nanoparticles which have a particle size from approximately 10 nm to approximately 50 nm.

Si is used herein to mean silicon dioxide, which is also commonly known as "silica."

It is to be understood that the discussions and examples herein are directed to the use of copper compounds as the active ingredient contained in silica nanoparticles that are used to form silica nanogel in a treatment for citrus canker. Applicant's invention is not limited to the use of copper compounds and the treatment of citrus canker, the scope of the invention is to broadly cover the use of silica based nanoformulations that serve as hosts for a broad array of fungicides/bactericides, including, but not limited to, metallic copper (Cu), copper salts, copper complexes, metallic zinc (Zn), zinc oxides, zinc salts, metallic silver (Ag), silver salts, silver complexes, titanium dioxide (Ti02), cerium oxides, magnesium oxides, zirconium oxides, polyethyleneimine (PEI), carbon, mixed carbon or soot, fullerenes, carbon nanotubes and the like.

The present invention involves a unique application of nanoscience and nanotechnology to develop engineered copper Cu(II) loaded silica nanogel (CuSiNG) material. The nanotechnology allows the manipulation of a silica nanoenvironment around Cu, establishing a sustained Cu ion release mechanism. The novel CuSiNP design shown in FIG. 2, allows association of copper (Cu) to silica NG in three different forms, enabling sustained Cu release. First, electrostatically bound Cu ions in the core 10. Second, covalently bound Cu in the hydrated particle surface 20 and nanopores 30. Third, surface bound Cu as hydroxide/oxide nanoclusters/nanoparticles 40. The nanogel structure consists of ultra-small nanoparticles (CuSiNPs) less than approximately 50 nm in diameter to provide better plant surface coverage and improved adherence properties. All these attractive features will form a solid basis for long-term protection of plants from pathogens using CuSiNG material.

Due to nanoscale engineering, the CuSiNG of the present invention has the following advantages over the existing Cu based compounds: uniform coverage of plant surface because of ultra-small particle size, better adherence property due to gel-like nanostructure, sustained (long-term) Cu release profile, better control on Cu release rate (adjustable "soluble" to "insoluble" Cu ratio), more antibacterial/antifungal activity with less amount of Cu content, reduced phytotoxic effect because of adjustable "soluble" to "insoluble" Cu ratio and environment-safe due to less Cu content, no harmful by-product formation, water-based synthesis, utilization of excess CuSiNG as plant nutrient and minimal possibility of having elevated local Cu concentration that could cause environmental toxicity.

The synthesis protocol has the following advantages: (i) simplicity, (ii) water-based, (ii) scalable to field applications, (iii) single-pot synthesis method, requiring no purification steps and (v) concentrated CuSiNG material could be easily diluted for field application. A non-technical person can do this task by adding an appropriate amount of water, thus reducing shipping costs. The method also uses inexpensive raw chemicals and is easily produced in a cost-effective manner.

Example 1

Synthesis of CuSiNG

Figure 3:
FIG. 3 is a transmission electron microscopy (TEM) image of copper, silica nanogel (CuSiNG) formulation consisting of silica nanoparticles approximately 10 nm in diameter that are interconnected.

The synthesis of the copper/silica nanogel (CuSiNG) was carried out at room temperature via one-step acid-catalyzed sol-gel process using tetraethoxysilane (TEOS), water, ethanol, and Cu(II) sulfate. Hydrolysis as shown below in equation 4 and condensation reactions in equations 5 and 6 below resulted in the formation of ultra-small (<10 nm size) Cu loaded silica nanopaticles (CuSiNPs). When maintained in acidic condition for several hours, gelation takes place. FIG. 3 shows formation of CuSiNG where CuSiNPs are interconnected.

$$(RO)_3SiOR + H_2O \rightarrow (RO)_3SiH + ROH \quad (4)$$

$$2(RO)_3SiOH \rightarrow (RO)_3Si-O-Si(OR)_3 + H_2O \quad (5)$$

$$(RO)_3SiOH + ROSi(OR)_3 \rightarrow (RO)_3Si-O-Si(OR)_3 + ROH \quad (6)$$

The overall synthesis process will involve two simple steps: First, the addition of Cu(II) salts to the acidic reaction medium in the beginning of nanoparticle synthesis and second, addition of a neutralizing agent, such as, sodium hydroxide (NaOH) after the synthesis to adjust the pH to 7.0. The acid reaction medium is formed with any inorganic acid, such as hydrochloric (HCl), sulfuric ($H_2SO_4$), nitric ($H_2NO_3$) and the like. The neutralizing agent is any compound with an alkaline pH, such as sodium hydroxide, ammonium hydroxide, potassium hydroxide and the like.

Gelation of sol particles will take place over time. The viscosity of the resulting gel can be easily controlled by adjusting the pH and timing between these two simple synthesis steps. This is a simple one-pot, a few hours long synthesis technique that requires no purification. Because of this simplicity, large scale, multi-ton scale production of CuSiNG is feasible. The process is environmentally-safe because it is a water-based "Green synthesis" technique, resulting in no harmful by-products, both silica and Cu are naturally found in the environment, CuSiNG will have "fixed" Cu at low levels, and CuSiNG will not elevate local Cu levels in the soil as it will be consumed as a plant nutrient. The method also uses readily available inexpensive chemicals for the synthesis of CuSiNG.

To study the binding of ionic Cu to SiNG, CuSiNG is synthesized in acidic pH reaction media, such as a 1% hydrochloric acid solution; however, a neutralizing agent is not added. The CuSiNG material is collected by centrifugation to remove the supernatant containing any free Cu ions. The CuSiNG is washed several times with deionized (DI) water. In this CuSiNG material, CuSiNP surface will be free of Cu hydroxide/oxide precipitate and Cu will be found only m its ionic form and is hereafter identified as "CuSiNP-clean."

Figure 1A:
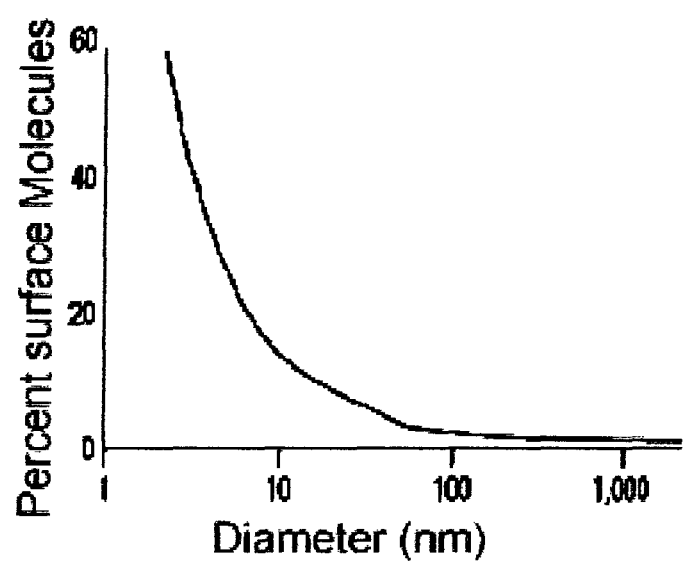
Figure 1B:
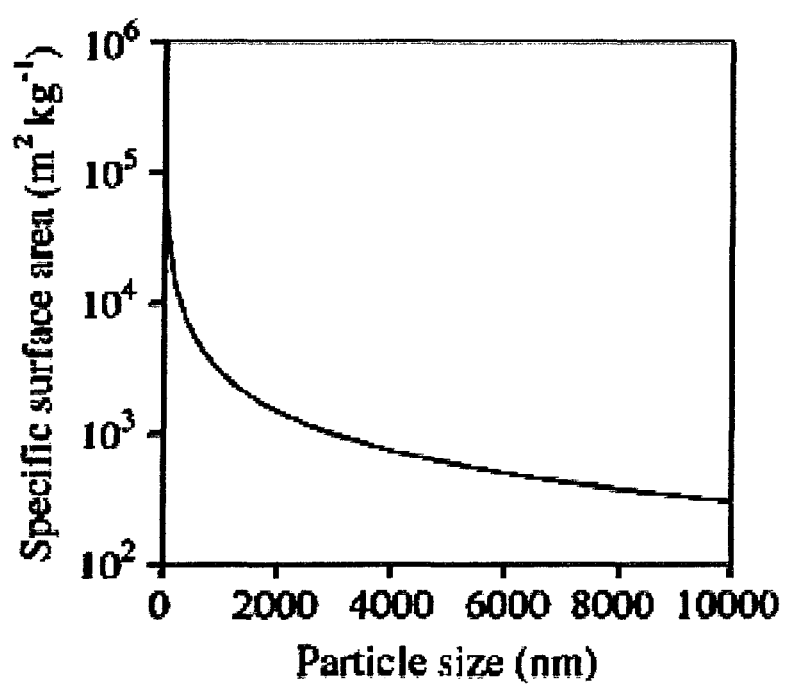
Figure 2:
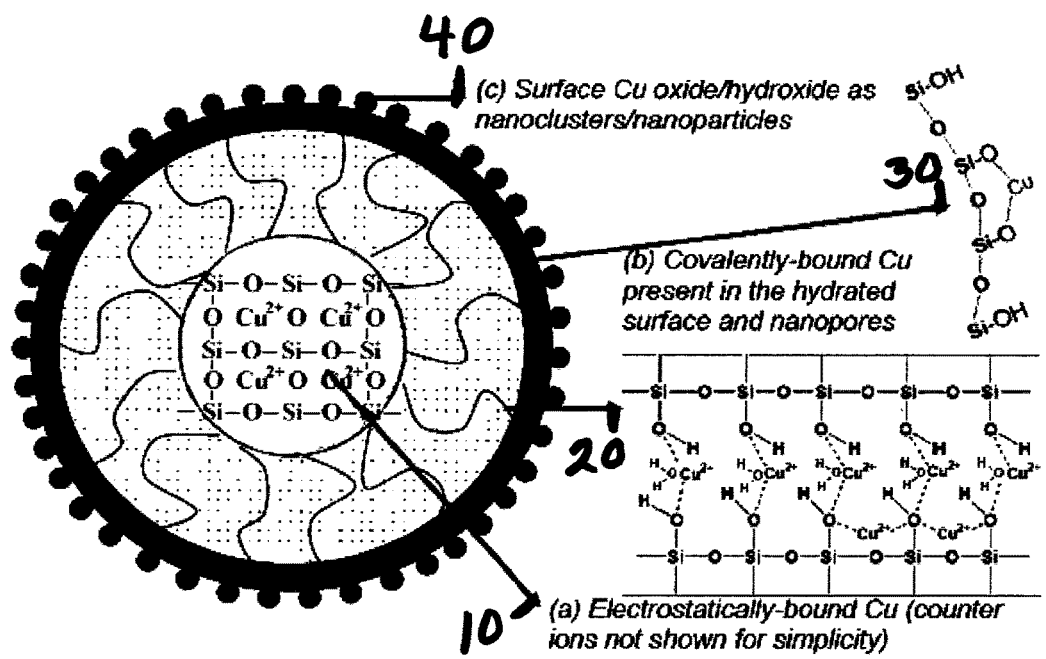

The CuSiNG (nanogel) consists of inter-connected ultra-small uniform size CuSiNPs (particles), as shown in FIG. 2, forming a gel-like structure, as shown in FIG. 3. These CuSiNPs will have core-shell nanostructure. The core 10 will consist of Cu ion loaded silica and the shell 20 will support Cu hydroxide/Cu oxide nanoclusters 40 that will be deposited on the surface of the shell 20. The CuSiNP size is tunable and the particle size is variable from 10 nm to 50 nm by controlling nucleation and growth process. The rationale of varying particle size is to control the surface to volume ratio. Larger size particle will have less surface area but more core volume. This will provide a unique opportunity to manipulate the ratio of ionic Cu in the CuSiNP core 20 to the surface-bound ionic Cu 40. It should also be noted that amorphous silica is highly porous, consisting of numerous hydrated nanochannels 30. The channel diameter is typically 1-2 nm. Water and ethanol molecules populate the plurality of nano-channels (bound via hydrogen bonding) and provide a unique nanoenvironment to Cu ions. It should be noted that the polarity and the hydrogen bonding capacity can be easily tuned within the nano-channel 30 by varying ethanol to water ratio, providing a good control over Cu ion release from the channels. The core 10 of the particle has a reduced polar environment and is deprived of solvent molecules. This environment will facilitate the formation of Cu salt nanocrystals where both Cu and sulfate ions will be present in a reduced polar environment, as shown in FIG. 2.

In CuSiNG, surface-bound ionic Cu will populate the particle surface as well as at the particle-particle interface. Therefore, the unique CuSiNP design provides three different Cu nanoenvironments, (i) electrostatically held core 10 Cu; i.e. ionic Cu at the NG core, (ii) covalently bound ionic Cu within nano-channels 30, at the particle surface 20 and at the interface and (iii) deposited Cu on the particle surface in its hydroxide/oxide form 40; the surface form 40 of Cu will be highly exposed to the surrounding environment. The Cu present in these three nanoenvironments will establish different Cu release kinetics that can be controlled in a sustained manner. The CuSiNG is expected to have very uniform coverage on plant surface due to smaller particle size. Again, much improved surface adherence property is expected because of gel-like nanostructure of CuSiNG (as it takes the advantage of combined adherence property of individual CuSiNPs in the network).

The novel CuSiNG design provides more soluble ("free and active") Cu for improved antifungal/antibacterial activity even though it will have less metallic Cu content per gram of material. During spray application in the field, some amount of CuSiNG will be deposited on the soil that will serve as Cu-based nutrient for the plant. Reduced Cu content in CuSiNG will thus be used for dual purposes; first as an essential micronutrient and secondly, as a fungicide/bactericide while minimizing Cu related toxicity in the environment.

Example 2

Binding of Copper to Silica Nanogel

The binding of Cu to SiNG was clearly evident from the blue color appearance of the product shown in FIG. 4a. The product is water-dispersible. Upon centrifugation, a blue residue was obtained and the supernatant was clear as shown in FIG. 4b. In contrast, silica NG when prepared in the absence of Cu ions showed characteristic white color of silica.

To evaluate how well Cu was bound to silica NG, CuSiNG was treated with ethylenediamine tetraacetic acid (EDTA), a strong chelator for Cu ions. Within several minutes, a water-soluble Cu-EDT A complex formed as shown in FIG. 4c. Upon centrifugation, we obtained white color residue of silica NG and blue color supernatant of Cu-EDTA complex as shown in FIG. 4d. These results clearly demonstrate that the binding of Cu to silica is not as strong as in Cu-EDTA complex. Therefore, the loaded Cu could be slowly released in its ionic form from the CuSiNG. CuSiNG Product Characterization.

Samples were characterized by transmission electron microscopy (TEM), X-ray diffraction (XRD), X-ray photoelectron spectroscopy (XPS), and energy dispersive spectroscopy (EDS).

Size

The size of CuSiNG was determined using transmission electron microscopy (TEM). The CuSiNG consisted of ultra-small (~10 nm) size inter-connected nanoparticles (NPs), forming a gel-like nanostructure as shown in FIG. 3. X-ray diffraction (XRD) was used to determine crystallinity (if any) for CuSiNG and compared the data with Kocide® 3000. XRD pattern clearly distinguishes CuSiNG from Kocide® 3000. As shown in the FIG. 5, Kocide® 3000 was primarily crystalline Cu hydroxide/oxide material whereas CuSiNG was purely amorphous in nature. The scanning electron microscopy-energy dispersive spectroscopy (SEM-EDS, an elemental analysis technique) showed that the amount of Cu (in atomic percentage, qualitative estimation) present in Kocide® 3000 and CuSiNG is 54 at. % and 13 at. %, respectively. The oxidation state of Cu in CuSiNG was determined by the X-ray photoelectron spectroscopy (XPS). XPS is able to provide information on the oxidation state of each component in the sample as well as the composition of the sample surface.

Binding Energy (eV)

High resolution regional spectra of the key elemental composition provide detailed individual component information such as chemical shift and intensity changes, indicating changes of bonding among individual elements. High-resolution XPS spectra of copper (Cu) 2p, oxygen (O) 1s and siica (Si) 2p3 are shown in FIG. 6. The Cu 2p peaks at binding energy 933.3 eV was attributed to the $CU^{2+}$ environment. Broad satellite peaks at higher binding energies also suggest the presence of $CU^{2+}$ ionic states. The higher binding energy component located at 935.2 eV was attributed to $Cu(OH)_2$ species. The O 1s and Si 2p3 peaks were located at binding energy of 532.1 eV and 103.1 eV respectively. The binding 5 energy of Si 2p matches well with the data published by National Institute of Standard and Technology of USA that is the Si in the CuSiNG sample is in the form of $SiO_2$.

Compositional Analysis

Semi-quantitative compositional analysis is possible by comparing XPS and EDS data, since XPS is a surface sensitive method and EDS is a bulk method of compositional analysis. The atomic ratios of Si!Cu from XPS and EDS were determined by integrating the peak areas and dividing by the sensitivity factors. The Si/Cu ratios from EDS and XPS data were identified as 2.3 and 7.3, respectively, confirming that Cu is distributed throughout the CuSiNG.

Antibacterial Activity

Assessment of antibacterial activity of CuSiNG was performed using *E. coli* as a model system. Disc diffusion assay, considered as one of the most common microbiological methods for the evaluation of potential antibiotic agents, was used to evaluate antimicrobial activity of CuSiNG material. Specifically, *E. coli* (strain 8739 from ATCC) grown on nutrient agar plates were incubated with filter paper discs containing equal volume and Cu concentration of aqueous solutions of either Kocide® 3000 50, Cu sulfate (pH 7) 60, CuSiNG (pH 7) 70 or pure silica nanoparticles (NPs) (pH 7) (not shown). After an overnight incubation at 37° C., we found that the CuSiNG exhibited very significant antimicrobial activity, as shown in FIG. 7a, and indicated by a marked zone of clearance extending away from the corresponding disc 70. Notably, the activity of the CuSiNG was more pronounced than that of the Cu sulfate solution on disc 60, as shown in FIG. 7b and Kocide® 3000 on disc 50, shown in FIG. 7c even though the Cu content in CuSiNG is about 4 times less than the Cu content in Kocide® 3000 (as determined by the SEM-EDS measurements). The area of no *E. coli* growth surrounding the filter paper disc 50 with Kocide® 3000 is approximately half the area of no E. coli growth for the disc 70 with CuSiNG, which confirms the efficiency of the CuSiNG formulation with one-fourth of the copper content, the CuSiNG formulation has twice the antimicrobial activity as Kocide® 3000. It should be noted that pure silica NG, prepared without the Cu ions, did not show any antibacterial activity.

Adherence Property

Assessment of the adherence property of CuSiNG was qualitatively evaluated on a lemon plant. The plant was obtained from a Home Depot® hardware store in Orlando, Fla. In a typical experimental procedure, a first spraying of an aqueous suspension of CuSiNG and Kocide® 3000 was uniformly sprayed at a distance of 6 inches over half a dozen preselected experimental leaves, assigned for each sample, using a hand-held spray bottle. The excess liquid dripped off the leaf surface. At this stage, digital images were taken of the leaf surface sprayed with Kocide® 3000, CuSiNP and CuSiNG, the adherence results are recorded in Table II below. The sprayed liquid was allowed to completely dry and again images were taken of the dried leaf surface sprayed with Kocide® 3000 and CuSiNG. About 2 hours later, natural rain water was sprayed continuously for approximately minutes onto the same experimental leaves and the leaves with a continuous spraying of rain water were allowed to dry completely. At this stage, digital images of the dry leaves having a first spraying of Kocide® 3000, CuSiNP and CuSiNG and a second spraying of rain water are evaluated visually for adherence of antibacterial/antifungal agent to the surface of the leaf. A scale of 1 to 5 is used to evaluate adherence.

1=1-5% antibacterial/antifungal composition is on the surface of the leaf;
2=6-15% of antibacterial/antifungal composition is on the surface of the leaf;
3=16-40% of antibacterial/antifungal composition is on the surface of the leaf;
4=41-75% of antibacterial/antifungal composition is on the surface of the leaf;
5=76-95% of antibacterial/antifungal composition is on the surface of the leaf.

TABLE II

Adherence of Antibacterial! Antifungal Composition to Leaf Surface

| PRODUCT | KOCIDE ® 3000 | CuSiNP | CuSiNG |
|---|---|---|---|
| First spraying (Product applied) | 5 | 5 | 5 |
| Drying | 4 | 4 | 5 |
| Second spraying (5 minutes rainwater) | — | — | — |
| Drying | 2 | 3 | 4 |
| Product on Leaf | 1 | 2 | 4 |

The results clearly indicate the superior adherence property of the CuSiNG suspension over Kocide® 3000. As expected, CuSiNG showed more uniform coverage on the leaf surface. Interestingly, the CuSiNG application to a lemon tree leaf withstood very well the heavy rain fall and thunderstorm that was experienced continuously for five days and is shown in FIG. 8; an enlarged image of a lemon tree leaf with a marbled and visually discernable protective covering of CuSiNG. Most of the Kocide® 3000 formulation washed away after a couple of minutes of rain water spray.

To further evaluate the adherence property of CuSiNG, a fluorescence technique was used. Lemon tree leaves were tagged with fluorescein isothiocyanate (FITC), a green emitting fluorescent dye. The dye covalently attached to the silica. The purpose of fluorescence tagging was to monitor the SiNG adherence property more sensitively using fluorescence measurements. An array of spots was created on the experimental leaf shown in FIG. 9a with fluorescent SiNG material and allowed to dry completely under a dark environment to avoid photo bleaching of FITC dyes.

Using a handheld UV light source (366 nm multiband excitation), green fluorescence spots from the leaf surface were clearly noticed before the rain water spraying. FIG. 9b is a drawing of the fluorescent image showing the fluorescent CuSiNG spots in the same pattern as the leaf in FIG. 9a.

After approximately 3 hours, natural rain water was sprayed for about 5 minutes onto the leaf in FIG. 9b, the spray was allowed to dry completely again in the dark and the dry leaf is shown in FIG. 9c, with several CuSiNG spots on the surface. Using a handheld UV light source (366 nm multiband excitation), green fluorescence spots from the leaf surface were clearly noticed after the rain water spraying. FIG. 9d is a drawing of the fluorescent image showing the fluorescent CuSiNG material still adhering to the leaf in FIG. 9c in a similar pattern as shown on the leaf in FIG. 9c. The fluorescent images in FIGS. 9b and 9d confirm that the CuSiNG material is not washed off the leaf when subjected to rain water spraying.

The huge surface area of the nanogel (NG) materials is indeed a contributing factor towards releasing adequate amount of "soluble" Cu. The silica-nanogel (SiNG) matrix is porous and the surface is highly hydrated, as disclosed by S. Santra et al. in "Fluorescence Lifetime Measurements to Determine the Core-Shell Nanostructure of FITC-doped Silica Nanoparticles: An Optical Approach to Evaluate Nanoparticle Photostability," *Journal of Luminescence*, 2006. 117 (1) pages 75-82. This silica matrix provides a unique environment, allowing the embedding of various metallic ions, as disclosed in U.S. Pat. No. 6,548,264 to Tan, et al, as well as molecules without a significant change in physical and chemical properties. Characterization studies clearly show that Cu ions are successfully embedded within silica matrix and the embedded Cu ions are released in a sustained manner.

The adherence and slow, sustained release of Cu ions provides several other benefits for the present invention. First, when applied to plants, trees and the like, the leaves and/or branches that fall to the ground provide copper, a highly desired nutrient for the soil and in very low levels that are not environmentally harmful. Also, when the plants and trees are harvested or removed from agricultural production, the treated vegetation can be used for mulch or composting and provided additional Cu nutrients as a fertilizer.

Another benefit involves controlling mold and mildew growth. The copper (Cu) loaded silica nanoparticle/nanogel formulations of the present invention have superior antibacterial/antifungal activity for treating areas that favor and foster the growth of mold and mildew; in addition, a single treatment remains effective for from at least two months to approximately six months because the release of ionic Cu occurs in a slow, sustained manner and in quantities that inhibit germination of fungal spores, the primary "seeds" responsible for dissemination and reproduction of the fungus or bacterium. Because the spore or cell removed from the current infection cycle does not mature nor reproduce in the presence of copper, the fungus or bacterium is effectively killed. Bathrooms, kitchens, interior and exterior areas of structures subject to warm, moist conditions remain free of unsightly mold and mildew when treated with the silica-based nanoformulation of the present invention.

In conclusion, for the first time, a sustained Cu release mechanism is provided using a uniquely designed copper (Cu) containing silica nanoparticle/nanogel (SiNP/NG) formulation. The silica-based nanoformulation finds immediate application for citrus canker treatment. Additional uses of antibacterial/antifungal compositions containing SiNP/NG are for general purpose antibacterial/antifungal agents in agriculture and horticulture, including, but not limited to use on vegetables, flowers, grass, other plants, household applications, fabrics, leathers, plastics, paints and the like. The nanotechnology-enabled CuSiNG design is a "revolutionary re-invention" of Cu for safe application in modem agriculture in the $21^{st}$ century.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method for treating a disease in a plant species comprising applying to the plant species a composition comprising a silica-based nanoformulation, wherein the composition comprises a plurality of copper ions embedded in a silica nanogel, wherein a plurality of interconnected nanoparticles of the nanogel comprise a plurality of copper ions electrostatically bound to a nanoparticle core, and wherein the silica nanogel provides a sustained ionic copper release mechanism.

2. The method of claim 1 wherein the source of the plurality of copper ions is from copper compounds selected from the group consisting of metallic copper, copper oxide, copper oxychloride, copper sulfate, copper hydroxide, and mixtures thereof.

3. The method of claim 1, wherein the plant is a member of the citrus species.

4. The method of claim 3, wherein the disease is citrus canker.

5. The method of claim 3, wherein the disease is caused by any species of *Xanthomonas*.

6. The method of claim 1, wherein the plurality of copper ions is released in a sustained manner for at least six months.

7. The method of claim 1, comprising spraying the composition on a leaf of said plant species.

8. The method of claim 1, comprising spraying the composition on a field comprising said plant species.

9. The method of claim 1, wherein a plurality of interconnected nanoparticles of the nanogel comprise a plurality of copper ions covalently bound to a hydrated shell surface and nanopores of the nanoparticle.

10. The method of claim 1, wherein a plurality of interconnected nanoparticles of the nanogel comprise a plurality of copper oxide/hydroxide as nanoclusters/nanoparticles bound to the surface of the nanoparticle.

11. The method of claim 9, wherein the source of the plurality of copper ions is from copper compounds selected from the group consisting of metallic copper, copper oxide, copper oxychloride, copper sulfate, copper hydroxide and mixtures thereof.

12. The method of claim 10, wherein the source of the plurality of copper ions is from copper compounds selected from the group consisting of metallic copper, copper oxide, copper oxychloride, copper sulfate, copper hydroxide and mixtures thereof.

13. The method of claim 9, wherein the plurality of copper ions is released in a sustained manner for at least six months.

14. The method of claim 10, wherein the plurality of copper ions is released in a sustained manner for at least six months.

15. The method of claim 3, wherein the plurality of copper ions is released in a sustained manner for at least six months.

* * * * *